(12) United States Patent
Giribona et al.

(10) Patent No.: US 12,396,926 B2
(45) Date of Patent: Aug. 26, 2025

(54) FLUIDIC GROUP AND RELATED APPARATUS FOR DRUG PREPARATION

(71) Applicant: BIOVALLEY GROUP S.P.A., Trieste (IT)

(72) Inventors: Paolo Giribona, Trieste (IT); Enrico Merlani, Trieste (IT); Bastiano Deschmann, Trieste (IT); Bostjan Parovel, Trieste (IT)

(73) Assignee: Biovalley Group S.P.A. (IT)

( * ) Notice: Subject to any disclaimer, the term of this patent is extended or adjusted under 35 U.S.C. 154(b) by 492 days.

(21) Appl. No.: 17/922,649

(22) PCT Filed: May 4, 2021

(86) PCT No.: PCT/IB2021/053733
§ 371 (c)(1),
(2) Date: Nov. 1, 2022

(87) PCT Pub. No.: WO2021/224791
PCT Pub. Date: Nov. 11, 2021

(65) Prior Publication Data
US 2023/0165754 A1 Jun. 1, 2023

(30) Foreign Application Priority Data
May 4, 2020 (IT) .......................... 102020000009751

(51) Int. Cl.
*A61J 1/20* (2006.01)
(52) U.S. Cl.
CPC ........... *A61J 1/2089* (2013.01); *A61J 1/2055* (2015.05); *A61J 1/2096* (2013.01)
(58) Field of Classification Search
CPC .............................. A61J 1/2089; A61J 1/2096
See application file for complete search history.

(56) References Cited

U.S. PATENT DOCUMENTS

| 10,925,808 | B2 * | 2/2021 | Pak | A61J 1/20 |
| 2015/0053305 | A1 * | 2/2015 | Davidian | A61J 1/22 |
| | | | | 141/2 |

(Continued)

FOREIGN PATENT DOCUMENTS

| WO | 2007/122209 | 11/2007 |
| WO | 2014/204894 | 12/2014 |

(Continued)

OTHER PUBLICATIONS

International Search Report and Written Opinion corresponding to International Patent Application No. PCT/IB2021/053733, mailed Jul. 2, 2021.

*Primary Examiner* — Timothy P. Kelly
(74) *Attorney, Agent, or Firm* — McAndrews, Held & Malloy, Ltd.

(57) ABSTRACT

A fluidic group couplable to a first container adapted to contain a drug and a second container adapted to contain an ingredient, comprising: a syringe comprising a movable piston defining a chamber having a variable volume; a first and a second coupling group selectively fixable to the second and, respectively, to the first container; a forking element having a first, a second and a third inlet in fluid communication with each other and, respectively, with the first coupling group, with the second coupling group and with the chamber; a first one-way valve interposed between the first coupling group and the forking element and controllable to allow the passage of the ingredient from the second container to the chamber; and a second one-way valve interposed between the second coupling group and the forking element and controllable to allow the passage of the ingredient from the chamber to the first container.

16 Claims, 8 Drawing Sheets

(56) References Cited

U.S. PATENT DOCUMENTS

2015/0087868 A1* 3/2015 Lee .................. C07B 59/00
                                                    422/159
2015/0283322 A1  10/2015 Hachey et al.
2022/0023531 A1* 1/2022 McLoughlin ..... A61M 5/14248
2022/0362106 A1* 11/2022 Gyory .................. A61J 1/2037

FOREIGN PATENT DOCUMENTS

WO    2015/071852    5/2015
WO    2017/096072    6/2017

* cited by examiner

FLUIDIC GROUP AND RELATED APPARATUS FOR DRUG PREPARATION

CROSS-REFERENCE TO RELATED APPLICATIONS

The present application is filed pursuant to 35 U.S.C. 371 as a U.S. National Phase application of International Patent Application No. PCT/IB2021/053733, which was filed May 4, 2021, claiming priority from Italian patent application no. 102020000009751 filed on Apr. 5, 2020. The entire text of the aforementioned applications is incorporated herein by reference in its entirety.

TECHNICAL FIELD

The present invention relates to a fluidic group and related apparatus for drug preparation.

BACKGROUND ART

As is well known, in the field of oncology, the ability to dose chemotherapy drugs precisely and individually for each patient is particularly critical. In fact, chemotherapy drugs used in cancer therapies can generate significant toxic effects, since they have a very narrow window of effective therapeutic concentration (or therapeutic range).

From an operational point of view, there are considerable criticalities in the process of preparation and management of cancer therapies, which is currently still largely based on manual operations by trained operators (e.g. medical staff and/or health professionals). This generates negative consequences in terms of risk for patients and operators, which are difficult to reconcile with an advanced and modern healthcare management.

In particular, the need to manually create chemotherapy drugs (e.g. by pipetting ingredients from respective containers and mixing them together to create the chemotherapy drug) increases the risk of drug contamination and preparation errors. In addition, the operators involved in these operations are exposed to the ingredients and drugs, with potentially negative consequences on their health due to the toxicity of the ingredients.

The main critical elements include the following:
  poor precision in the formulation of cancer drugs due to human error;
  need to provide in-depth education and specific training to operators in charge of dosing chemotherapy drugs;
  difficulty in managing unused quantities of extremely expensive drugs;
  high occupational risk for operators involved in the preparation of chemotherapy drugs.

DISCLOSURE OF INVENTION

Aim of the present invention is to provide a fluidic group and related apparatus for drug preparation which solve the disadvantages of the known art.

According to the present invention, a fluidic group and related apparatus for drug preparation, as defined in the appended claims, are realised.

BRIEF DESCRIPTION OF THE DRAWINGS

For a better understanding of the present invention, a preferred, non-limiting embodiment thereof is described below, provided by way of non-limiting example and in a triaxial Cartesian system XYZ with reference to the accompanying drawings, wherein.

BEST MODE FOR CARRYING OUT THE INVENTION

In particular, the figures are shown with reference to the triaxial Cartesian system XYZ defined by an X axis, a Y axis and a Z axis, orthogonal to each other. Next, a gravity acceleration acting along the Z axis is considered.

In the description below, elements common to the various embodiments of the invention are indicated with the same reference numbers.

Figure 1:
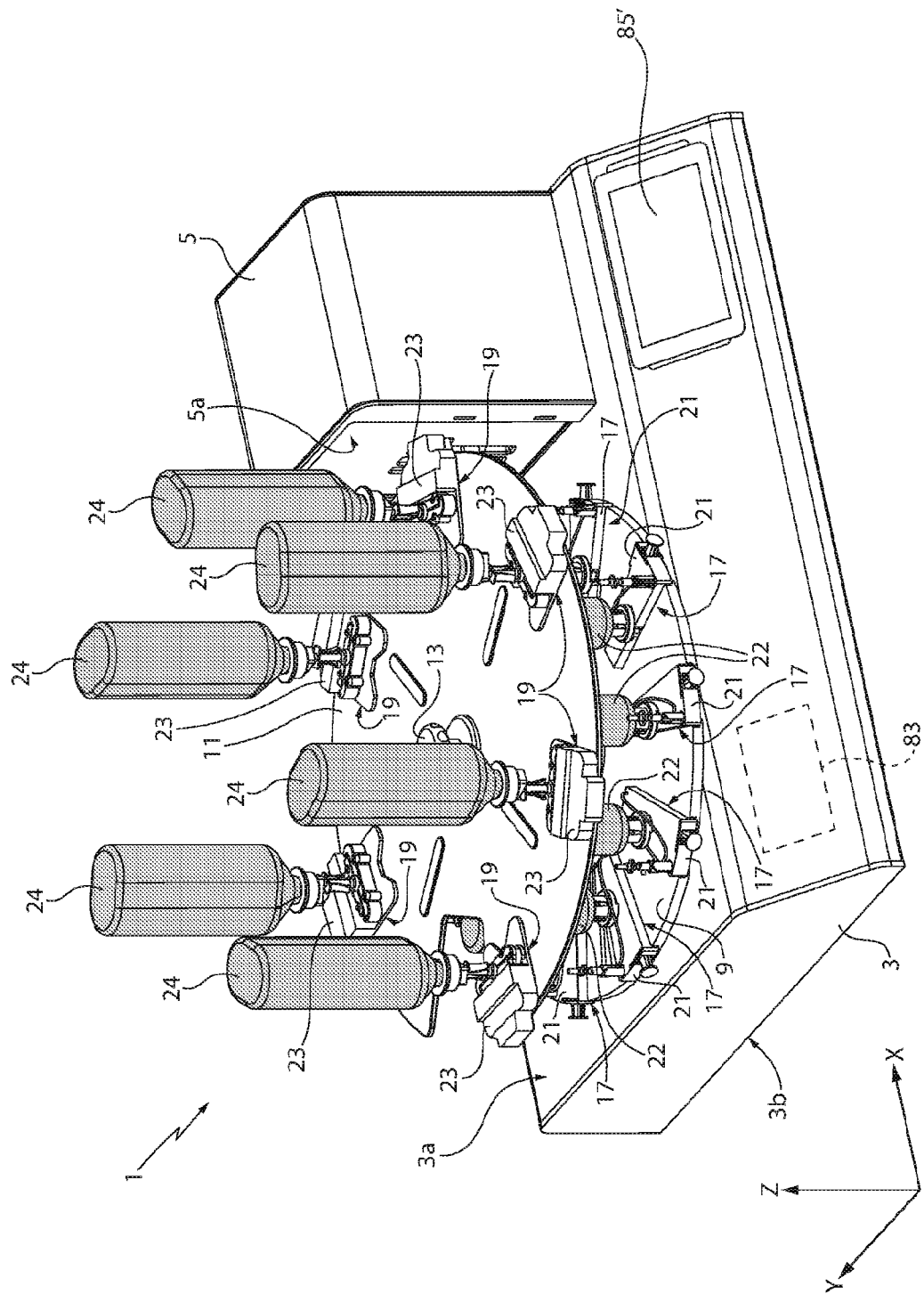
FIG. 1 is a schematic perspective view of an apparatus for the preparation of chemotherapeutic drugs, according to an embodiment.
Figure 1A:
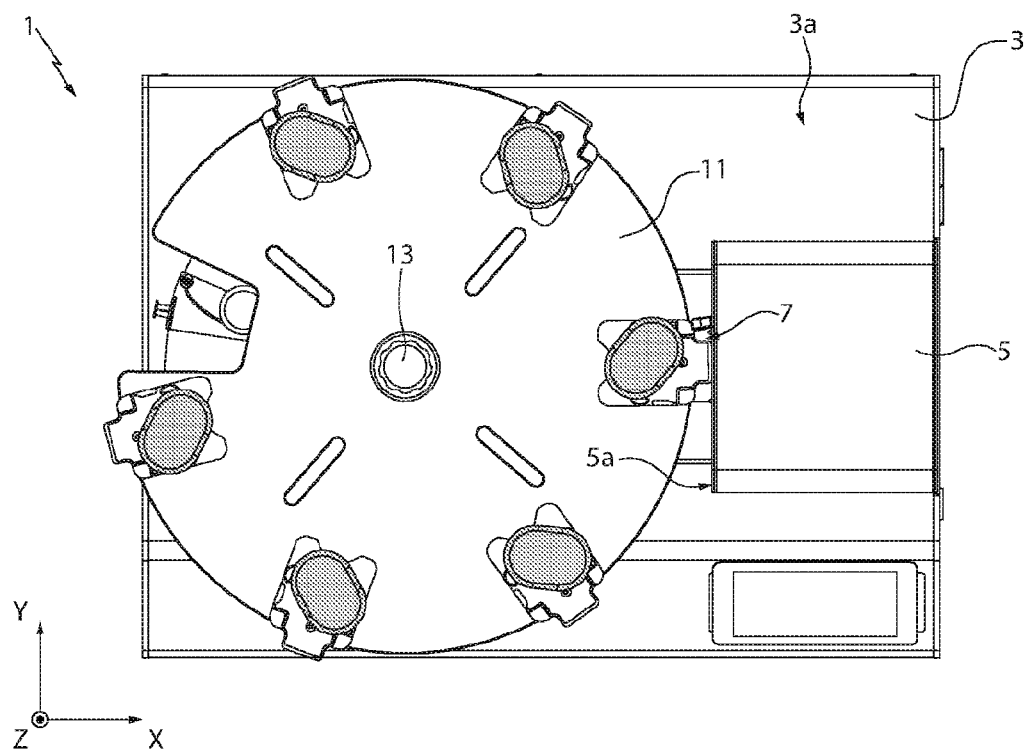
FIG. 1A is a schematic view from above, in an XY plane, of the apparatus of FIG. 1.
Figure 1B:
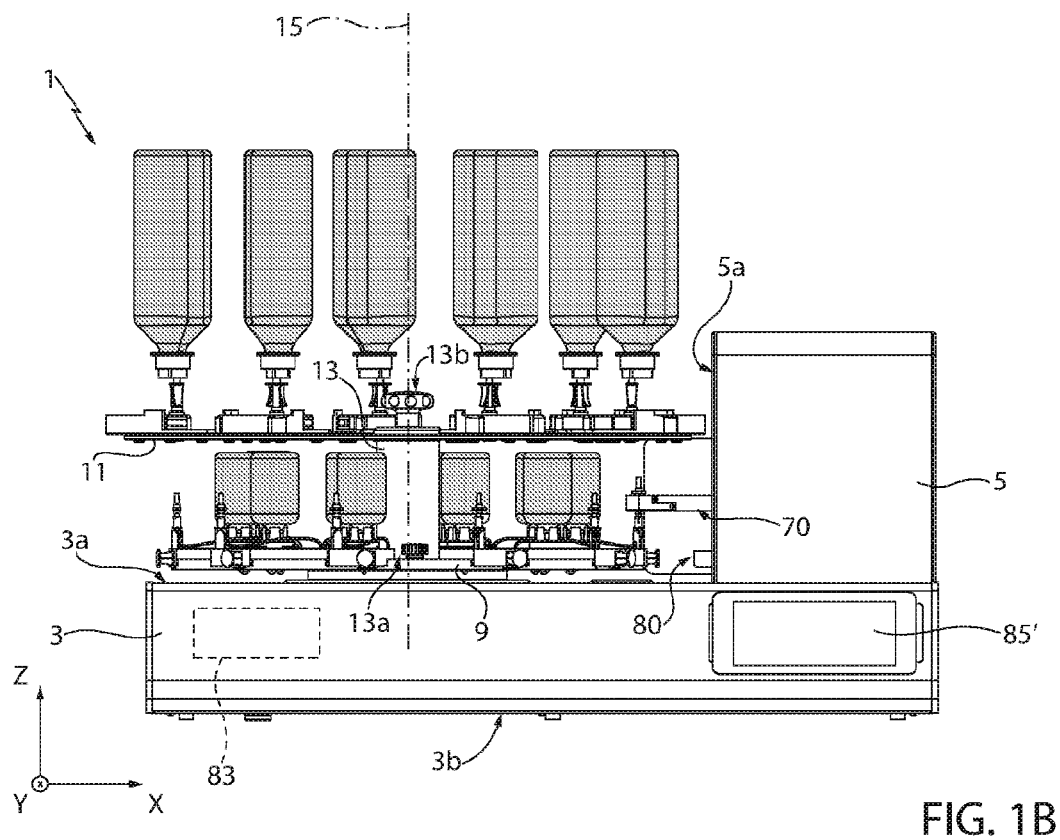
FIG. 1B is a schematic side view, in an XZ plane, of the apparatus of FIG. 1.

FIGS. 1, 1A and 1B show an apparatus for preparation of chemotherapy drugs (hereafter referred to as "apparatus" and indicated by reference number 1).

The apparatus 1 includes a base 3 configured to be placed on a support (not shown, such as a table, a piece of furniture or a platform), and in particular on a surface (not shown) of the support extending in a horizontal XY plane defined by the axes X and Y. The base 3 has an upper surface 3a and a lower surface 3b opposite each other along the Z axis, and extending substantially parallel to each other and parallel to the XY plane.

A first rotor 9 and a second rotor 11 are carried by the base 3 and have a substantially flat shape. In particular, the first and the second rotor 9, 11 have a main extension in the XY plane and have a substantially flat circular shape in the XY plane. The rotors 9, 11 are arranged superimposed one upon the other, are coaxial to each other and are coupled to the base 3 by means of a central stator 13 fixed to the upper surface 3a, extending perpendicularly to said surface 3a and arranged centrally to the rotors 9, 11. In detail, the stator 13 of rectilinear shape has main extension along a rotation axis 15 parallel to the Z axis and includes for example a rod. The stator 13 has a first lower end (not shown) and a second upper end 13b, opposite each other along the Z axis, and is fixed to the base 3 by the first lower end. The rotors 9, 11 are coupled to the stator 13 in a per se known manner, for example by means of respective bearings (not shown), and are configured to rotate with respect to the stator 13. In detail, the stator 13 is arranged centrally with respect to the rotors 9, 11 which rotate, in respective rotation planes (parallel to the XY plane), with respect to the rotation axis 15 (orthogonal to the rotation planes). The rotors 9, 11 are therefore placed at different levels along the Z axis, and in particular the first (lower) rotor 9 faces the upper surface 3a of the base 3 and is at a distance from said upper surface 3a, along the Z axis, a distance which is less than the distance shown by the second (upper) rotor 11. In other words, the first lower rotor 9 is interposed, along the Z axis, between the base 3 and the second upper rotor 11.

The first rotor 9 includes a plurality of first seats 17 each configured to house a respective fluidic device 21, better described below. Each fluidic device 21 is coupled to a respective first fluidic container 22 (hereinafter, first container 22). In particular, each first container 22—of known type—includes a first body 22a (e.g., bottle, vial, ampoule) defining a first internal volume and having a through opening closed by a first cap 22b (e.g., of silicone). Each first container 22 is adapted to contain a respective ingredient, and is releasably coupled (e.g., by interlocking) to the respective fluidic device 21 at the cap 22b, as better described below. In detail, the first containers 22 and the respective fluidic devices 21 are arranged, angularly equally spaced apart between them, at an outer edge of the first rotor 9.

The second rotor 11 includes a plurality of second seats 19 configured to house a respective plurality of supports 23. In particular, each support 23 is releasably coupled to the respective second seat 19. Each support 23 includes a first surface 23a and a second surface 23b (FIG. 5A) opposite to each other along the Z axis, and includes a respective second portion (extending at the second surface 23b) shaped so as to releasably fit into the respective second seat 19, for example by interlocking in order to fix the support 23 to the respective second seat 19. The second surfaces 23b of the supports 23 thus face the second rotor 11. Each support 23 is releasably coupled to a respective second fluid container 24 (hereinafter, second container 24) also of known type. In particular, each second container 24 includes a second body 24a (e.g., bottle, vial, ampoule) defining a second internal volume and having a through opening closed by a second cap 24b (e.g., of silicone). Each second container 24 is adapted to contain a respective chemotherapeutic drug to be administered to a respective patient. Each second container 24 is releasably coupled (e.g., by interlocking) to the respective support 23 at the cap 22b. Thus, each cap 22b faces the first surface 23a of the respective support 23. In detail, the second containers 24 and the respective supports 23 are arranged, angularly equally spaced apart between them, at an outer edge of the second rotor 11.

The second rotor 11 has a larger diameter than the respective diameter of the first rotor 9.

An operating device 5 is coupled (in particular, fixed) to the upper surface 3a of the base 3. The operating device 5 has a side wall 5a facing the rotors 9, 11.

The operating device 5 comprises first operating means (not shown), of a type known per se and configured to allow rotation of the rotors 9, 11 with respect to the stator 13. According to an embodiment, the first operating means extend starting from the side wall 5a. Each rotor 9, 11 is independently operated such that the rotors 9, 11 can rotate independently of each other, with different speeds and/or with opposite angular directions (e.g., clockwise and counterclockwise in the top view of FIG. 1B) and with different angular speeds. For example, the first operating means 27 comprise a first and a second motorised gear (not shown, such as gear wheels). The first motorised gear is configured to engage a first toothing fixed to the first rotor 9 (e.g., fixed to a perimeter surface of the first rotor 9); the second motorised gear is configured to engage a second toothing fixed to the second rotor 11 (e.g., fixed to a perimeter surface of the second rotor 11). Alternatively, the first operating means 27 comprise a first and second belt drive configured to cooperate frictionally with the first and, respectively, second rotor 9, 11 (e.g., with the side surfaces of the rotors 9, 11). Alternatively, the first operating means 27 exploit, in a per se known manner, electromagnetic fields to move the rotors 9, 11. Alternatively, the first operating means 27 are included in the base 3 and the stator 13 includes respective drive means to actuate the rotors 9, 11. Alternatively, the first operating means 27 are based on direct drive technologies.

Figure 3:
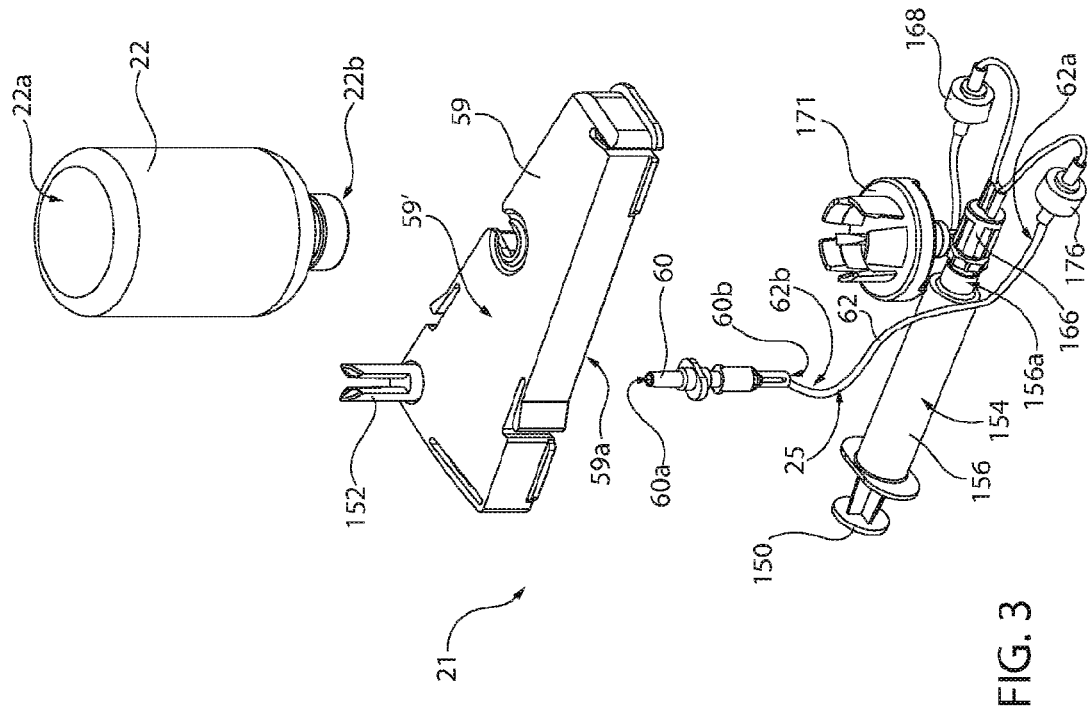
FIG. 3 is a schematic exploded view of the fluidic device of FIG. 2.
Figure 2:
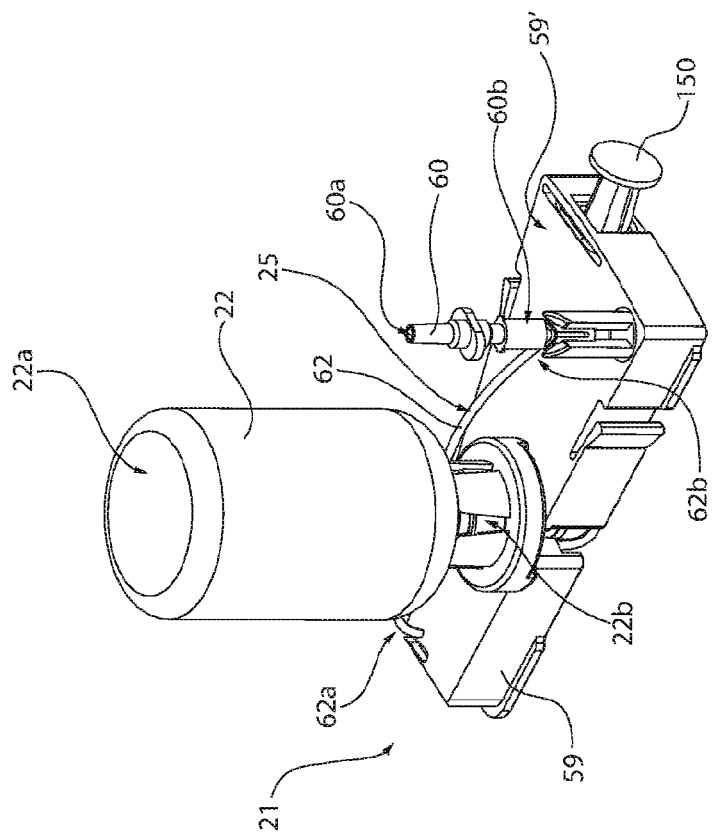
FIG. 2 is a schematic perspective view of a fluidic device included in the apparatus of FIG. 1, according to an embodiment.
Figure 4:
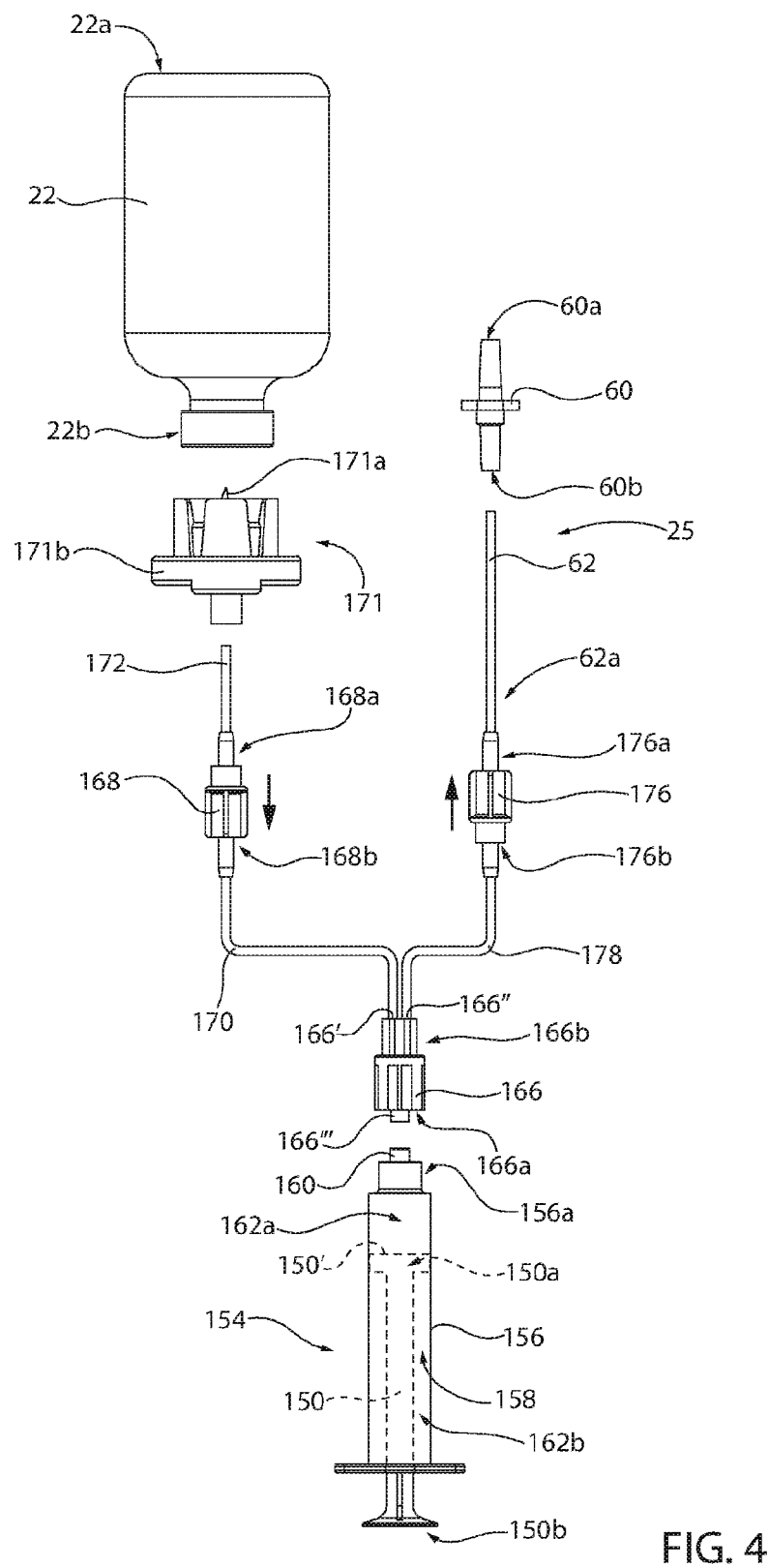
FIG. 4 is a schematic exploded view of a detail of the fluidic device of FIG. 2.

FIGS. 2-4 show one of the fluidic devices 21 in detail. The fluidic device 21 includes a main body 59 shaped so as to releasably couple with (e.g., fit into) the respective first seat 17, for example by interlocking so as to releasably fix the fluidic device 21 to the respective first seat 17.

The fluidic device 21 comprises a fluidic connection means 25 fixed to the main body 59 and adapted to fluidically connect the first container 22 with the second container 24. The fluidic connection means 25 includes a first hollow needle 60 (hereinafter, also referred to as first needle 60 and having a first and second end 60a, 60b) and a first tubular element 62 (e.g., of plastic material and having a first and second end 62a, 62b). The first needle 60 is configured to be coupled to (e.g., inserted into) the second cap 24b through the first end 60a, as better described below. The first tubular element 62 is flexible, is coupled to the main body 59 through the first end 62a and is coupled, through the second end 62b, to the second end 60b of the first needle 60. The first tubular element 62 and the first needle 60 are coupled to each other so as to allow a passage of fluid from the main body 59 through the first tubular element 62 and the first needle 60. In detail, the first tubular element 62 has a first through opening defined between the ends 62a, 62b, and the first needle 60 has a second through opening defined between the ends 60a, 60b. The first and second cavity face each other at the second ends 60b, 62b.

The first needle 60 is supported, in a releasable manner, by a first support portion 152 of the main body 59, and is movable, as shown below, with respect to the main body 59. In detail, the first support portion 152 extends starting from, and perpendicularly to, a surface 59' of the main body 59, said surface 59' being facing the containers 22, 24 when the latter are coupled to the main body 59. When coupled together, the first support portion 152 supports the first needle 60 so that the second end 60b of the first needle 60 is facing the main body 59 (at the surface 59'), and so that the first end 60a of the first needle 60 is facing the first container 22. Furthermore, in use the fluidic device 21 and the support 23 considered are mutually arranged so that the first needle 60 is facing the second cap 24b along the Z axis.

The main body 59 has a housing cavity 59a in which a syringe 154 comprising a hollow body 156 is housed (in detail, inclusive). The body 156 defines a cavity 158 having a polygonal (e.g. circular) cross-section. The body 156 includes an end 156a having a through opening 160. Internally to the cavity 158 there is a plunger (or piston) 150, movable (e.g., cooperating with sliding) with respect to the body 156 and operable so as to generate a pressure gradient (e.g., at the through opening 160). In detail, the piston 150 is movable, longitudinally to the body 156, in the cavity 158 and has a first and second end 150a, 150b opposite each other. The piston 150 comprises, at the first end 150a, a seal element 150' sliding in a fluid-tight manner in the body 156 (in detail, it slides along an internal surface of the body 156, facing said cavity) thus defining a first and a second chamber 162a, 162b having a variable volume in the cavity 158. The chambers 162a, 162b are fluid-tightly separated from each other by the seal element 150' and have respective volumes that are variable as a function the axial position assumed by the piston 150 with respect to the body 156. In detail, the first chamber 162a is in fluid communication with the outside of the syringe 154 via the through opening 160 located at the end 156a. For example, the piston 150 is movable from a first position (of compression of the first chamber 162a) to a second position (of expansion of the first chamber 162a): in the first position, the seal element 150' is at the end 156a and the piston 150 is almost completely housed in the cavity 158, and therefore the first chamber 162a has a volume smaller than the volume of the second chamber 162b (in other words, the seal element 150' has a first distance $D_1$ from the end 156a of the body 156, and the first chamber 162a has a first volume); and in the second position, only the seal element 150' is in the cavity 158 and the piston 150 is almost completely outside the body 156, and therefore the first chamber 162a has a volume greater than the volume of the second chamber 162b (in other words, the seal element 150' has a second distance $D_2$ from the end 156a of the body 156, and the first chamber 162a has a second volume, the second distance $D_2$ being greater than the first distance $D_1$ and the second chamber being greater than the first chamber 162b).

The syringe 154 is coupled to the first container 22 by means of a forking element 166 and a first one-way (non-return, or check) valve 168 (hereinafter, first valve 168), that are also arranged in the housing cavity 59a. The first valve 168 has a first and a second end 168a, 168b opposite to each other, and is operable in an opening state and, alternatively, in a closing state as a function of a first force caused by a first pressure difference between said ends 168a, 168b. The first pressure difference is a function of a first pressure gradient present at the first valve 168, which in turn is related to said pressure gradient in the through opening 160. In fact, the forking element 166 and the first valve 168 are in pneumatic communication with the through opening 160 of the syringe 154. In a rest condition, the first valve 168 is in the closing state; when, on the other hand, the pressure gradient in the through opening 160 is directed towards the cavity 158 (i.e. towards the inside of the syringe 154) and has an absolute value greater than a first threshold (in other words, when the first force acting on the first valve 168 is greater than a threshold force), the first valve 168 passes from the closing state to the opening state, allowing a passage of fluid only from the first container 22 towards the syringe 154 (thus preventing a passage of fluid from the syringe 154 towards the first container 22), and then returns to the closing state when the pressure gradient in the through opening 160 is exhausted. On the other hand, the forking element 166 allows the passage of fluid, coming from the syringe 154, along a first and a second fluidic path, as better described below.

In detail, the forking element 166 has a first and second end 166a, 166b opposite each other. At the second end 166b, the forking element 166 has a first and second fluidic channel 166', 166" and, at the first end 166a, the forking element 166 has a third fluidic channel 166'''. The fluidic channels 166', 166", 166''' have a Y-arrangement between them (i.e. they are joined and fluidically connected to each other in a connection portion). The through opening 160 of the syringe 154 is coupled to (e.g., fixed to, and in fluid communication with) the first end 166a of the forking element 166 (in detail, to the third fluidic channel 166'''). For example, the syringe 154 and the forking element 166 are coupled to each other directly or through a further tubular element (not shown and analogous to the first tubular element 62).

Further, the first fluidic channel 166' of the second end 166b is coupled to (e.g., fixed to, and in fluid communication with) the second end 168b of the first valve 168 through a second tubular element 170 (analogous to the first tubular element 62). The first end 168a of the first valve 168 is coupled to (e.g., fixed to, and in fluid communication with) the first cap 22b. In particular, the first end 168a is coupled to (e.g., fixed to, and in fluid communication with; e.g., directly or through a third tubular element 172 analogous to the first tubular element 62) an interface means 171 that is releasably couplable to the first container 22.

The interface means 171 is placed, at least partially, externally to the housing cavity 59a and includes a second support portion 171b. The second support portion 171b is fixed to the main body 59, is external to the housing cavity 59a and, when the first container 22 is coupled to the fluidic device 21, is releasably fixed to the second cap 22b so as to physically support and sustain the first container 22. The second support portion 171b includes a second hollow needle 171a (hereinafter, second needle 171, analogous to the first needle 60) configured to be coupled to (e.g., inserted into) the first cap 22b. In detail, when the first container 22 is supported by the second support portion 171b, the second needle 171a is inserted into the first cap 22b thereby allowing fluidic communication between the first container 22 and the syringe 154.

The forking element 166, the second tubular element 170, the first valve 168, the interface means 171 and, if any, the third tubular element 172 define the first fluidic path, which therefore crosses the first and third fluidic channel 166', 166''' to fluidically connect the first internal volume and the first chamber 162a with each other.

A second one-way (non-return, or check) valve 176 (hereinafter, second valve 176) is interposed between the fluidic connection means 25 and the forking element 166. The second valve 176 has a first and a second end 176a, 176b opposite each other, and is operable in an opening state and, alternatively, in a closing state as a function of a second force caused by a second pressure difference between said ends 176a, 176b. The second pressure difference is a function of a second pressure gradient present at the second valve 176, which in turn is related to said pressure gradient in the through opening 160. In fact, the forking element 166 and the second valve 176 are in pneumatic communication with the through opening 160 of the syringe 154. In a rest condition, the second valve 176 is in the closing state; when, however, the pressure gradient in the through opening 160 is directed towards the forking element 166 (i.e., towards the outside of the syringe 154) and has an absolute value greater than a second threshold (e.g., equal to the first threshold; in other words, when the second force acting on the second valve 176 is greater than a further threshold force), the second valve 176 passes from the closing state to the opening state, allowing a passage of fluid only from the syringe 154 towards the first needle 60, and therefore towards the second container 24 (thus preventing a passage of fluid from the second container 24 towards the syringe 154), to then return to the closing state when the pressure gradient in the through opening 160 is exhausted.

In detail, the second fluidic channel 166" of the second end 166b is coupled to (e.g., fixed to, and in fluid communication with) the second end 176b of the second valve 176 through a fourth tubular element 178 (analogous to the first tubular element 62). The first end 176a of the second valve 176 is coupled to (e.g., fixed to, and in fluid communication with) the first end 62a of the first tubular element 62. The second valve 176 and the fourth tubular element 178 are also included in the housing cavity 59a.

The forking element 166, the fourth tubular element 178, the second valve 176 and the fluidic connection means 25 define the second fluidic path, which therefore crosses the second and the third fluidic channels 166", 166'" to fluidically connect the first chamber 162a and the second internal volume with each other.

More in detail, the fluidic device 21 comprises the following elements, which are assembled together (e.g. by gluing) so as to form a single group adapted to transfer liquids without leakage:

the interface means 171: this is a ventilated spike, adapted to pierce the first cap 22b (i.e. an elastomer cap normally present in drug bottles) and to withdraw the ingredient from the first selected container 22, with compensation of the internal pressure of the first container 22 (the spike is provided with a double lumen: one through which the ingredient is withdrawn from the first container 22, the other allowing the entry into the first container 22 of air in equal volume, in order to compensate for the pressure inside the first body 22a);

the first valve 168 and the second valve 176: these are one-way valves, each allowing the ingredient to pass only in the direction indicated by the respective arrow in FIG. 4;

the forking element 166: it is a "Y" fitting, provided with a luer-lock connector for connection to the syringe 154;

the syringe 154: this is a luer-lock syringe;

the first needle 60: it is a male, non-valved luer-slip connector, suitable for connection to female luer-slip or luer-lock connectors, whether or not valved; and the first tubular element 62, the second tubular element 170, the third tubular element 172 and the fourth tubular element 178: these are respective connection tubes between the various elements mentioned above, as described in more detail above.

Figure 5A:
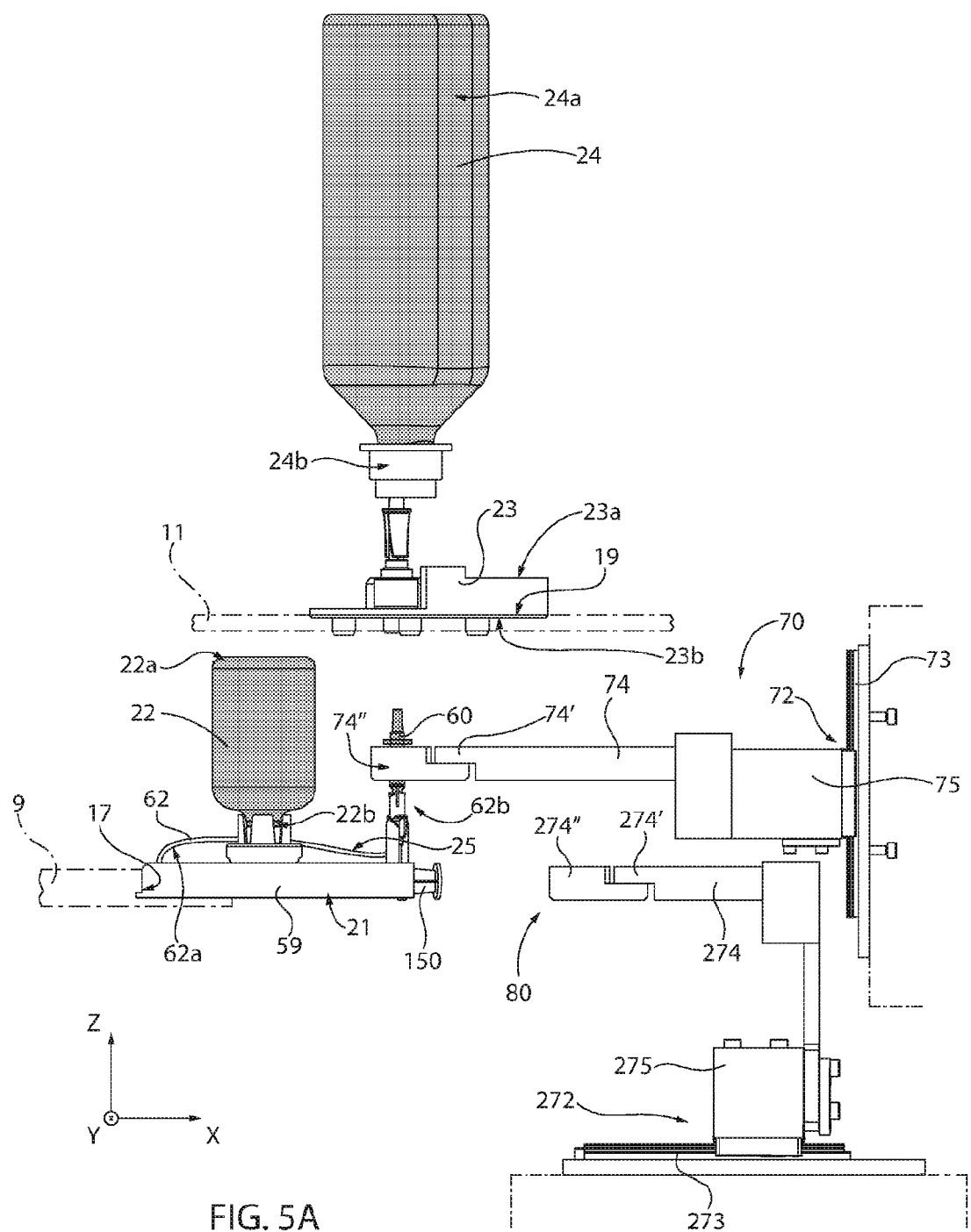
FIGS. 5A-5D are schematic side views, in the XZ plane, of a detail of the apparatus of FIG. 1 in respective operating modes, this detail including the fluidic device of FIG. 2.

With reference to FIGS. 1B, 5A, the operating device 5 further comprises second operating means 70, configured to move the first needle 60 by displacing it upwards (thus towards the rotor 11 along the Z axis) so as to couple the first needle 60 of the fluidic device 21 with the second cap 24b of the second container 24 considered. In particular, the second operating means 70 extend starting from the side wall 5a, and include a first translation means 72 and a first gripping means 74, operatively coupled to each other.

The first gripping means 74 is configured to couple to the first needle 60, allowing for the aforesaid movement. In particular, the first gripping means 74 includes two arms 74' having respective end portions 74". For example, the arms 74' have main extension parallel to the X axis, are arranged so that the first needle 60 is placed, parallel to the Y axis, between these end portions 74", and the arms 74' can be operated so that they are closed around the needle 60 and allow it to be seized. In a first operating condition, the end portions 74" are decoupled from each other (they are arranged with each other along the Y axis at a first distance $D_1$); and in a second operating condition, the end portions 74" are coupled with each other (they are arranged with each other along the Y axis at a second distance $D_2$ less than the first distance $D_1$). In particular, in the second operating condition, the end portions 74" abut with the first needle 60, which is therefore integral with the end portions 74" by friction and/or interlocking with the latter. The arms 74' are operated in a manner per se known (e.g., by means of gears, by means of a motor, e.g., a stepper type, or by means of at least one translation means defining a respective path parallel to the Y axis and analogous to the first translation means 72 described below).

The first translation means 72 is configured to displace the first needle 60 with respect to the main body 59 towards the second rotor 11. The first translation means 72 comprises a first guide element 73 and a first movable element 75, which are movable between them (e.g., cooperating with each other by sliding). In particular, the first guide element 73 is fixed to the side wall 5a and has main extension parallel to the Z axis. In other words, the first guide element 73 defines a first path along which the first movable element 75 is constrained to move, said first path being linear and parallel to the Z axis. In detail, the first guide element 73 extends, along the Z axis, from the level of the first needle 60 to the level of the cap 24b.

The first movable element 75 is moved in the first guide element 73 by means of first motor means (not shown). In particular, the first motor means are fixed to the side wall 5a or to the first guide element 73, and are coupled to the first movable element 75 so as to allow it to be displaced in the first guide element 73 from a rest position to an activation position. For example, the first motor means include a first stepper motor, or linear actuators based on geared motors, or actuators of the pneumatic or hydraulic type.

The subsequent actions of the first gripping means 74 and the first translation means 72 thus make it possible to seize the first needle 60 arranged in the rest position and, subsequently, to displace it parallel to the Z axis until bringing it into the activation position in which the first needle 60 is inserted into the second cap 24b, thus allowing a fluidic connection between the first container 22 and the second container 24.

The operating device 5 further comprises third operating means 80 (or pumping means), configured to operate the fluidic device 21 so as to allow a passage of fluid between the first container 22 and the first needle 60. In particular, the third operating means 80 are controllable to operate the piston 150 in order to pump fluid from the first container 22 to the second container 24.

For example, the third operating means 80 extend starting from the side wall 5a, and include a second translation means 272 and a second gripping means 274, operatively coupled to each other.

The second gripping means 274 is configured to couple to the piston 150 at the second end 150b. In particular, the second gripping means 274 includes two respective arms 274' having respective end portions 274". For example, the arms 274' have main extension parallel to the X axis, are available such that the second end 150b of the piston 150 is available, parallel to the Y axis, between these end portions 274", and the arms 274' can be operated so that they are closed around the piston 150 and allow it to be seized. In a first operating condition, the end portions 274" are decoupled from each other (e.g., they are arranged with each other along the Y axis at a third distance $D_3$); and in a second operating condition, the end portions 274" are coupled with each other (e.g., they are arranged with each other along the Y axis at a fourth distance $D_4$ less than the third distance $D_3$). In particular, in the second operating condition, the end portions 274" abut with the second end 150b of the piston 150, which is therefore integral with the end portions 274" by friction and/or interlocking with the latter. The arms 274' are operated in a manner per se known (e.g., by means of gears, by means of a motor, e.g., a stepper type, or by means of at least one translation means defining a respective path parallel to the Y axis and analogous to the first translation means 72).

The second translation means 272 is configured to displace the piston 150 with respect to the main body 59; this displacement of the piston 150 occurs, alternately, towards the side wall 5a and towards the main body 59. The second translation means 272 comprises a second guide element 273 and a second movable element 275, which are movable between them (e.g., cooperating with each other by sliding). In particular, the second guide element 273 is fixed to the side wall 5a and has main extension parallel to the X axis. In other words, the second guide element 273 defines a second path along which the second movable element 275 is constrained to move, said second path being linear and parallel to the X axis.

The second movable element 275 is moved in the second guide element 273 by means of second motor means (not shown). In particular, the second operating means are fixed to the side wall 5a or to the second guide element 273, and are coupled to the second movable element 275 so as to allow it to be displaced in the second guide element 273 from a first position (e.g., in which the piston 150 is in the compression position of the first chamber 162a) to a second position (e.g., in which the piston 150 is in the expansion position of the first chamber 162a), and vice versa. For example, the third motor means include a third stepper motor, or linear actuators based on geared motors, or actuators of the pneumatic or hydraulic type.

The subsequent actions of the second gripping means 274 and the second translation means 272 thus make it possible to seize the piston 150 arranged in the compression position of the first chamber 162a and, subsequently, to displace it parallel to the X axis until it is brought into the expansion position of the first chamber 162a, and vice versa. This makes it possible to create said pressure gradients, to actuate the valves 168, 176 and to transfer part of the ingredient from the first container 22 to the second container 24, as better described below.

A control unit 83 (such as a processor, ASIC, PCB, or dedicated controller) is also operatively coupled to the apparatus 1 and is configured to command the apparatus 1, and in particular to command the first operating means 27, the second operating means 70, and the third operating means 80. In particular, the apparatus 1 includes the control unit 83 (e.g., the control unit 83 is included in the base 3 or in the operating device 5).

Optionally, the apparatus 1 further comprises first interface means 85', for example including at least one between a display device (such as a screen, also of the touch screen type) and a plurality of buttons. For example, the first interface means 85' are included in the base 3 or in the operating device 5. In addition, the apparatus 1 may also be operatively coupled (e.g., wired, via the Internet or electromagnetically) to second interface means 85" (not shown), such as external electronic devices (e.g., computer, smartphone, keyboard or mouse). In particular, the second interface means 85" may include a printing apparatus, such as a label printer. In particular, the first interface means 85' and the second interface means 85" are operatively coupled to the control unit 83.

With reference to FIGS. 5A-5D and 6, a method for operating 100 the apparatus 1, implemented via the control unit 83, is described.

The operating method 100 starts at step 102. Initially, the supports 23, the fluidic devices 21 and the containers 22, 24 are not coupled to the apparatus 1. At step 102, the device 1 is turned on and acquires prescription data which are entered, either by the operator or in an automated manner, via the first interface means 85' and/or second interface means 85" (e.g., a server of a hospital facility comprising an archive with patient data). The prescription data are indicative of the prescription to be followed, i.e. the chemotherapy drug to be prepared for the patient under consideration. In particular, the prescription data include:

- patient's personal data (name, surname, date of birth, any additional identifying information);
- active substance (or ingredient) of the chemotherapeutic drug to be prepared;
- quantity of active substance (or ingredient) prescribed;
- trade name and size (e.g. expressed in mL) of the second container 24 adapted to contain the chemotherapeutic drug;
- type of second container 24 (e.g. bag, syringe, elastomer);
- any substance already present in the second container 24 (e.g. in the case of bags) and relative volume; and
- delivery times.

For example, this quantity of active substance of the chemotherapy drug is delivered in weight $W_{pa}$ (e.g., in mg), and is converted into a corresponding weight $W_{fc}$ of commercial chemotherapy drug (e.g., in mg) using the following relationship:

$$P_{fc} = \frac{P_{pa}}{c_{fc}} \cdot d_{fc}$$

where $W_{fc}$ is the weight (in mg) of the chemotherapy drug to be dosed and administered to the patient under consideration, $W_{pa}$ is the weight (in mg) of the active substance (or ingredient), $d_{fc}$ is a density (in mg/mL) of the chemotherapy drug and cfc is a concentration of the active substance (or ingredient) in the chemotherapy drug.

In step 102, a set-up of the apparatus 1 is also performed, for example performed in a controlled atmosphere (e.g., under a hood) and including:

- disinfection and cleaning of apparatus 1, of the supports 23, of the fluidic devices 21 and of the containers 22, 24; and
- assembly of the supports 23, of the fluidic devices 21 and of the containers 22, 24 to the apparatus 1.

In particular, said assembly of the supports 23, of the fluidic devices 21 and of the containers 22, 24 to the apparatus 1 is performed by the operator or in an automated manner, and allows loading all the materials and/or objects necessary for the preparation of the specific chemotherapeutic drug. The supports 23, the fluidic devices 21 and the containers 22, 24 are identified by reading respective identification codes associated therewith. In particular, the supports 23, the fluidic devices 21 and the containers 22, 24 have either respective labels glued thereto and including respective barcodes, or respective radio frequency identification ("RFID") labels, suitable for identifying them. The fluidic devices 21 and the first containers 22 are releasably fixed to each other, and then the fluidic devices 21 carrying the first containers 22 are coupled to the first rotor 9, as previously described. Similarly, the supports 23 and the second containers 24 are releasably fixed to each other, and then the supports 23 carrying the second containers 24 are coupled to the second rotor 11, as previously described.

This is followed, at a step 104, by a positioning of the rotors 9, 11, shown in FIG. 5A. In detail, the second rotor 11 rotates, by means of the first operating means 27, so as to bring the second selected container 24 closer to the operating device 5, said second container 24 being adapted to contain the chemotherapeutic drug of the patient under consideration. Furthermore, the first rotor 9 rotates, by means of the first operating means 27, so as to bring the selected first container 22 closer to the operating means 5, said first container 22 containing the ingredient to be inserted into the second container 24 to make the chemotherapeutic drug for the patient under consideration. The selected containers 22, 24 are therefore overlapping and at least partially aligned with each other parallel to the Z axis and face the side wall 5*a* of the operating device 5.

Figure 5C:
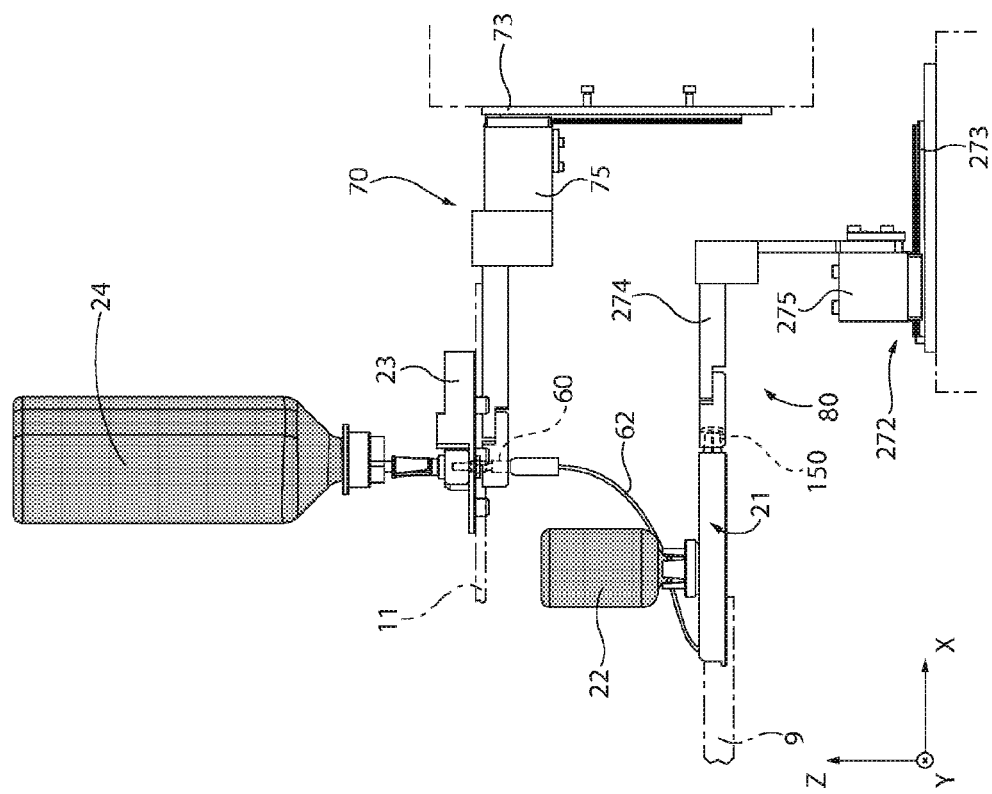
Figure 5B:
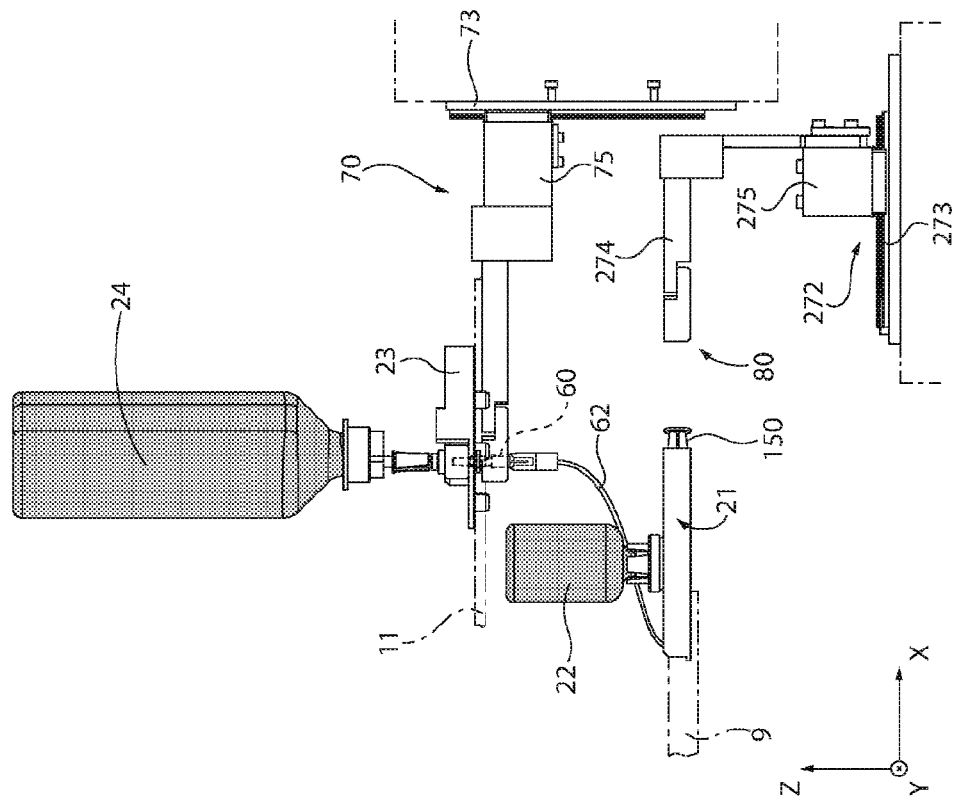

As shown in FIG. 5B, at a step 106, consecutive to step 104, the second operating means 70 couple the first needle 60 of the selected fluidic device 21 with the second selected container 24, said first needle 60 is used to achieve fluidic communication between the containers 22, 24 that have been selected.

As shown in FIG. 5C, at a step 108, consecutive to step 106, the third operating means 80 are coupled to the fluidic device 21, as further described below.

Figure 5D:
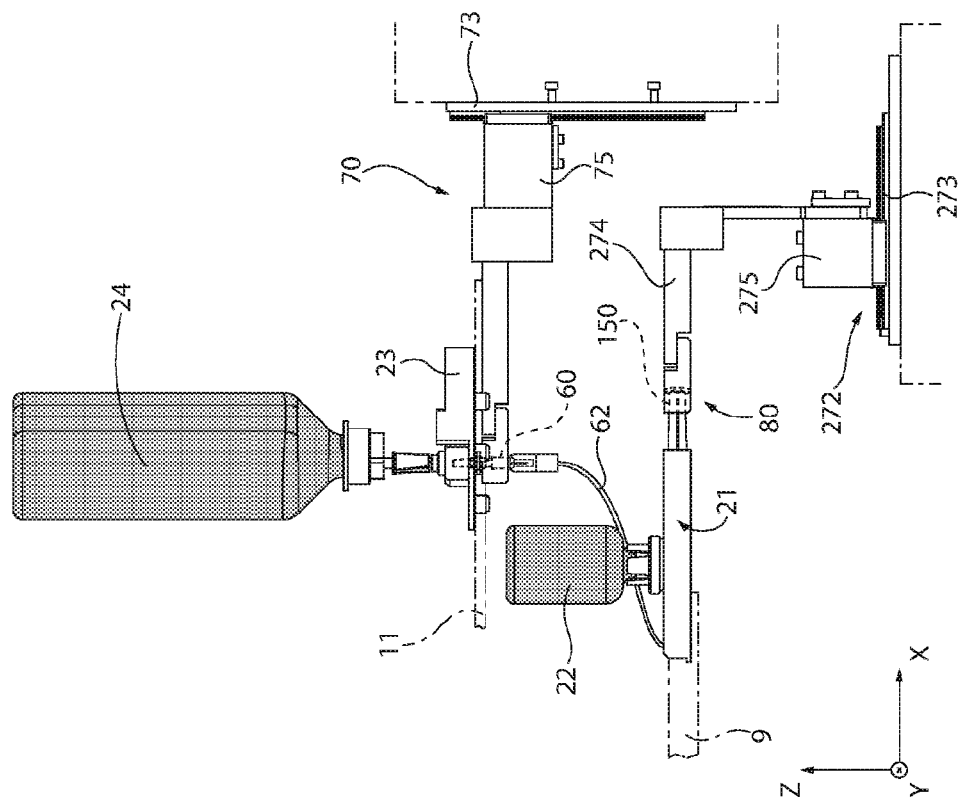
Figure 6:
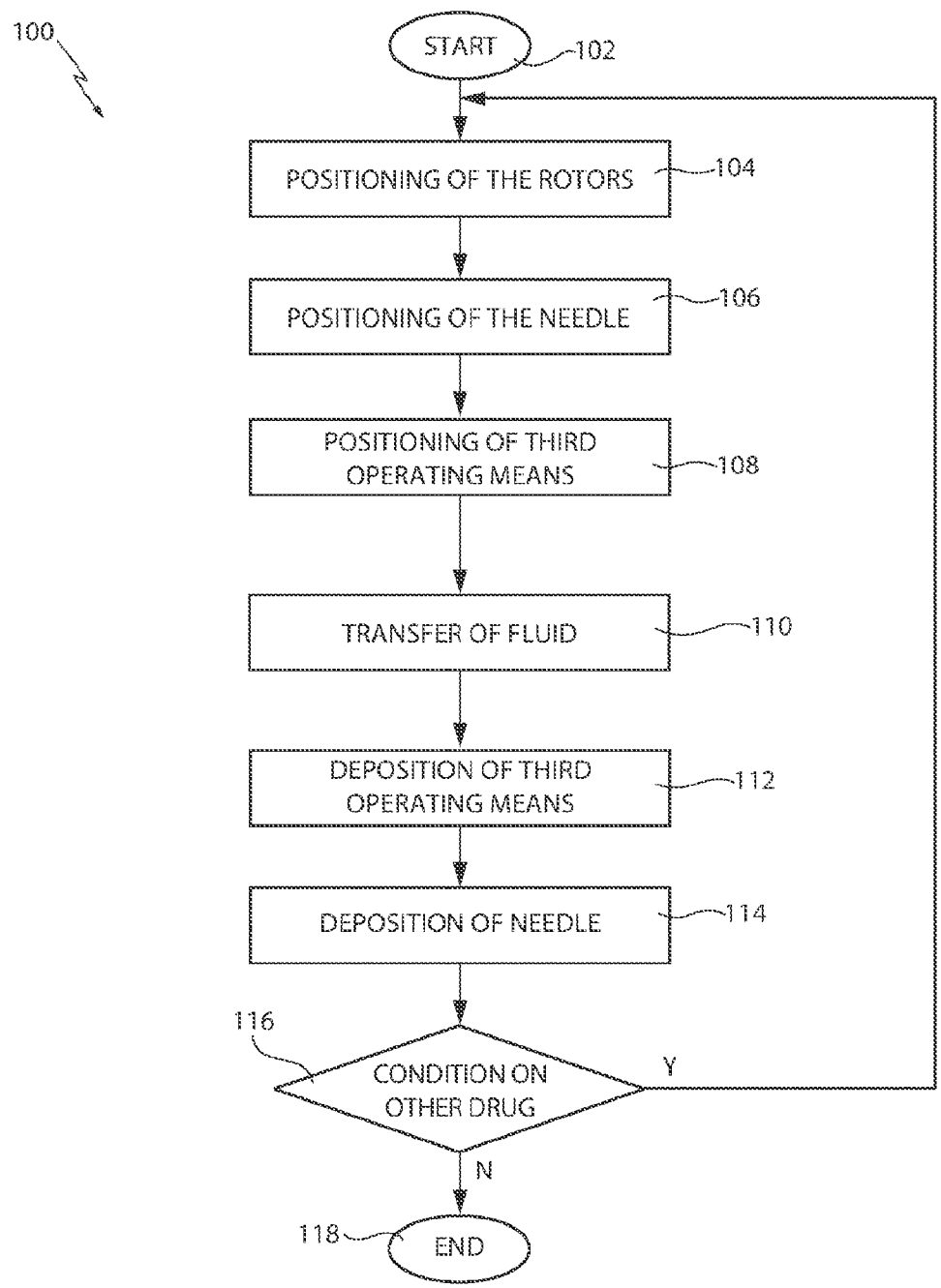
FIG. 6 is a block diagram showing a method of implementing the apparatus of FIG. 1.

As shown in FIG. 5D, at a step 110, consecutive to step 108, fluid is transferred from the first container 22 to the second container 24, as better described below.

At a step 112, consecutive to step 110, the third operating means 80 are decoupled from the fluidic device 21, performing a reverse movement to that described with reference to step 108 and, hereinafter, FIG. 5C.

At a step 114, consecutive to step 112, the second operating means 70 displace the first needle 60 downwards (i.e. in the direction of the base 3 along the Z axis) and decouple the first needle 60 from the second container 24, interrupting fluidic communication between the containers 22, 24. In other words, a reverse movement to that described with reference to step 106 is made.

At step 116, consecutive to step 114, a condition on the composition of the chemotherapeutic drug to be prepared is verified. In particular, it is determined whether other ingredients (located in respective first containers 22 other than the previously considered first container 22) need to be added to the second container 24 to obtain the chemotherapeutic drug.

If further ingredients are needed for the preparation of the chemotherapeutic drug (output "S" from step 116), the positioning of the rotors 9, 11 is performed again, thus returning to step 104. In particular, the first rotor 9 is operated to select the first container 22 of interest.

If no further ingredients are needed for the preparation of the considered chemotherapeutic drug (output "N" from step 116), the operating method 100 ends at a step 118, wherein, for example, the device 1 is turned off or will be awaiting a further order for a different preparation.

Furthermore, at step 118, a disassembly of the supports 23, of the fluidic devices 21 and of the containers 22, 24 from the apparatus 1 may be performed by the operator or in an automated manner, in order to prepare the apparatus 1 to perform step 102 again.

Furthermore, at step 118, an identification label for the second container 24 may be generated, for example, by means of said printing apparatus (included in the second interface means 85" and operatively coupled to the control unit 83). In particular, such a label may include, for example, a barcode label or an RFID label. Such a label is adapted to be coupled (e.g., glued or fixed) to the second container 24, and is indicative of data such as the nature of the chemotherapeutic drug contained in the second container 24 (e.g., chemical composition and/or active substance contained) and/or an identifier of the patient to whom said chemotherapeutic drug is to be administered.

In more detail and with reference to FIGS. 5B-5D, the operation of the third operating means 80 (shown here in their respective operating modes) is described.

In FIG. 5B, the third operating means 80 are in a position decoupled from the piston 150, and are therefore in a rest position.

In FIG. 5C, the third operating means 80 are coupled to the piston 150 (step 108). In particular, the second translation means 272 translates along the X axis the second gripping means 274 so that the second end 150*b* of the piston 150 is interposed, parallel to the Y axis, between the end portions 274". Subsequently, the second gripping means 274 is coupled to the piston 150, placing the end portions 274" in the second operating condition so that they are releasably fixed to the second end 150*b* of the piston 150.

In FIG. 5D, the third operating means 80 cause part of the ingredient to be transferred from the first container 22 to the syringe 154. In detail, the second translation means 272 translates along the X axis the second gripping means 274 and the piston 150, thus moving the first end 150*a* of the piston 150 away from the end 156*a* of the body 156. In other words, it passes from the compression position of the first chamber 162*a* to the extension position of the first chamber 162*a*. This generates the first pressure gradient (and thus lower pressure at the second ends 168*b*, 176*b* than at the first ends 168*a*, 176*a*) which brings, when the first force is greater than the threshold force, the first valve 168 into the opening state (while the second valve 176 remains in the closing state). Furthermore, the first pressure gradient causes, together with the force of gravity, the transfer of the ingredient from the first container 22 to the first chamber 162*a* of the syringe 154.

Similarly to the foregoing, a movement (not shown) of the third operating means 80 opposite to that shown in FIG. 5D causes the transfer of part of the ingredient from the syringe 154 to the second container 24. In detail, with reference to the configuration shown in FIG. 5D, the second translation means 272 translates again along the X axis the second gripping means 274 and the piston 150 in the opposite direction with respect to the moment described with reference to FIG. 5D, thus bringing the first end 150*a* of the piston 150 closer to the end 156*a* of the body 156. In other words, there is a passage from the expansion position of the first chamber 162*a* to the compression position of the first chamber 162*a*. This generates the second pressure gradient (and thus greater pressure at the second ends 168*b*, 176*b* than at the first ends 168*a*, 176*a*) which brings, when the second force is greater than the further threshold force, the second valve 176 into the opening state (while the first valve 168 remains in the closing state). In addition, the second pressure gradient causes the transfer of the ingredient from the first chamber 162*a* of the syringe 154 to the second container 24.

In conjunction with each other, the expansion and compression movements of the first chamber 162*a* operated by the third operating means 80 allow the transfer of the ingredient from the first container 22 to the second container 24 (step 110).

From an examination of the characteristics of the invention realised according to the present invention, the advantages that it allows obtaining are evident.

The apparatus 1 is an automated system for the preparation of anticancer drugs, capable of overcoming the critical elements connected with the manual preparation thereof and of ensuring a substantial increase in the quality of cancer therapies. In fact, the apparatus 1 allows a significant increase in formulation accuracy, a significant reduction of chemical contamination of the environments intended for the preparation of such drugs and a drastic reduction of the professional risk for the healthcare workers assigned thereto.

In addition, the apparatus 1 implements, via the control unit 83, a computerised procedure for managing chemotherapy preparations, for use for example by hospital pharmacies. This computerised procedure can be interfaced with a hospital information system (if any) through standard communication protocols.

The apparatus 1 is an automated table-top device, which can be easily inserted into a laminar flow hood for chemotherapy. For example, the apparatus 1 may be operated under a vertical laminar flow hood of ISO class 5, which in turn is placed in an ISO class 8 air-controlled environment.

Advantageously, the communication between the control unit 83 and the second interface means 85" takes place in wireless mode, in order to eliminate any wired connection between a sterile interior of the hood in which the apparatus 1 is positioned and the external environment.

In particular, the apparatus 1 allows the adoption of a closed circuit fluidic system able to guarantee sterility during the transfer of the chemotherapeutic drug from the first container 22 to the second container 24, and the absence of contamination of the surrounding environment.

In particular, the fluidic device 21 is made of low-cost plastic materials for medical use, such as polystyrene, polycarbonate, polyurethane or PVC and has a structure that is easy to manufacture. This ensures reduced manufacturing costs and allows for single use, of the disposable type. In other words, the fluidic device 21 is coupled only once to the respective first container 22, and after the transfer of the respective ingredient it is thrown away. This significantly reduces the risk of contamination for patients and healthcare workers.

The fluidic device 21 is a standardised interface allowing the coupling of different types of first containers 22 to the first rotor 9.

In addition, the chemotherapy drug is dosed directly into the second containers 24, which are the final containers intended for administration to the patient. This avoids the need for further and subsequent handling, which could be a source of further contamination.

Each second container 24 is identified by a code (e.g. QR) with the details of the chemotherapy drug preparation and of the patient for whom it is intended. This information is therefore verifiable at the time of administration in order to prevent possible accidental exchange of drugs.

The main advantages obtainable by means of apparatus 1 are:
increase in the accuracy of chemotherapy drug dosing;
increase in the sterility level of injectable preparations;
reduction of cytostatic contamination of the surrounding environment (laboratory, pharmacy, hospital);
more safety for hospital pharmacy workers (reduced needlestick injuries, reduction of hand fatigue pathologies, etc.);
more patient safety thanks to the reduction of the risk of accidental drug and/or patient exchanges, or incorrect dosing;
optimisation of the use of cytostatic drugs, with a reduction in the significant costs related to discarding unused cytostatic drugs; and
simplification of the drug preparation process, reducing machine set-up times.

In addition, the fluidic group 21 allows the connection, commanded by the second operating means 70 of the apparatus 1, between the first container 22 (i.e. the bottle with the selected ingredient) and the second container 24 (or final container of the drug, i.e. bag, syringe, etc.), aimed at transferring the ingredient itself in the predetermined quantity controlled by the apparatus 1.

As regards the first container 22, this connection with the fluidic group 21 is permanent and is consequent to the perforation of the first cap 22b by the interface means 171 and to the engagement of the metal capsule of the first cap 22b by a ring nut (e.g., of plastic) of the interface means 171.

As regards the second container 24, this connection with the fluidic unit 21 is made by means of the second operating means 70, which provide for the insertion of the first needle 60 (i.e., a non-valved male luer-slip connector) into a female Luer-lock connector (valved) previously coupled to the second container 24 (in detail, inserted into the second cap 24b).

In particular, the first needle 60 makes it possible to use the fluidic device 21 in the automated apparatus 1.

It is clear that changes and variations can be made to the invention described and shown herein without departing from the protection scope of the present invention, as defined in the appended claims.

In particular, the first operating means 27 may also be arranged in the base 3 instead of in the operating means 5.

In addition, the second rotor 11 may be replaced by a support structure (not shown) fixed to the base 3 (therefore not rotatable) in the event that only a second container 24 can be coupled to the apparatus 1. In such a case, after the ingredients have been added to the second container 24 to create the chemotherapeutic drug in a manner similar to that described above, said second container 24 is removed and replaced, automatically or manually, with a further second container 24 to proceed to a further preparation of chemotherapeutic drug.

The apparatus 1 may also be used in the preparation of drugs other than chemotherapeutic drugs, for example injectable drugs such as monoclonal antibodies, cytotoxics, hormones and hormone antagonists, antimitotics, alkylating agents, antibiotics.

The invention claimed is:

1. A fluidic group (21) couplable to a first container (24) defining a first internal volume adapted to contain a drug, and to a second container (22) defining a second internal volume adapted to contain an ingredient for the preparation of said drug, the fluidic group comprising a first body (59) defining a first cavity (59a) and including:
   a syringe (154) comprising a second body (156) defining a second cavity (158) housing a piston (150) movable in the second body (156) and defining, with the second body (156), a chamber (162a) having a variable volume as a function of a position of the piston (150) in the second cavity (158);
   a first coupling group (171, 172) extending partially outside the first cavity (59a) and fixable in a releasable manner to the second container (22) so as to be in fluid communication with the second internal volume;
   a second coupling group (25) extending partially outside the first cavity (59a) and fixable in a releasable manner to the first container (24) so as to be in fluid communication with the first internal volume;
   a forking element (166) having a first (166') and a second (166") inlet arranged in fluid communication with the first coupling group (171, 172) and, respectively, with the second coupling group (25), and furthermore having a third inlet (166''') in fluid communication with said chamber (162a), the third inlet further communicating with the first and second inlets so as to create a first fluidic path between the second internal volume and said chamber (162a) and a second fluidic path between said chamber (162a) and the first internal volume;

a first valve (168) of one-way type, interposed along the first fluidic path between the first coupling group (171, 172) and the forking element (166) and controllable, according to a first pressure gradient caused by a movement of the piston (150) in the cavity (158), to allow the passage of the ingredient from the second container (22) to the chamber (162a) of the syringe (154); and a second valve (176) of one-way type, interposed along the second fluidic path between the second coupling group (25) and the forking element (166) and controllable, as a function of a second pressure gradient opposite the first pressure gradient, to allow the passage, from said chamber (162a) to the first container (24), of the ingredient transferred from the second container (22) into the chamber (162a) of the syringe (154).

2. The fluidic group according to claim 1, wherein the second body (156) has a first (156a) and a second (156b) end portion opposite each other, the chamber (162a) being fluidically connected to the third inlet (166''') at said first end portion (156a), wherein the piston (150) comprises a seal element (150') defining with the second body (156) said chamber (162a) and sliding in a fluid-tight manner in the second body (156) between a first position and a second position relative to the second body (156), wherein, when the seal element (150') is in the first position, the seal element (150') has a first distance from the first end portion (156a) of the second body (156) and the chamber (162a) has a first volume, and wherein, when the seal element (150') is in the second position, the seal element (150') has a second distance from the first end portion (156a) of the second body (156) and the chamber (162a) has a second volume, the second distance being greater than the first distance and the second volume being greater than the first volume.

3. The fluidic group according to claim 1, wherein pumping means (80) are couplable in a releasable manner to the piston (150) and are operable to generate the first pressure gradient or the second pressure gradient by moving the piston (150) in the second cavity (158).

4. The fluidic group according to claim 2, wherein the first valve (168) is operable to pass from a first closing state to a first opening state and the second valve (176) is operable to pass from a second closing state to a second opening state, and wherein, when the seal element (150') is moved by the pumping means (80) from the first position to the second position, the first pressure gradient exerts a force such that the first valve (168) is in the first opening state and the second valve (176) is in the second closing state, and when the seal element (150') is moved by the pumping means (80) from the second position to the first position, the second pressure gradient exerts a further force such that the first valve (168) is in the first closing state and the second valve (176) is in the second opening state.

5. The fluidic group according to claim 1, wherein the second coupling group (25) comprises a first flexible tubular element (62) and a first hollow needle (60) fluidically coupled with the second valve (176) through said first tubular element (62), the first hollow needle (60) being movable with respect to the first body (59) and insertable in a first cap (24b) of the first container (24) so as to allow said fluid communication between said chamber (162a) of the syringe (154) and the first internal volume.

6. The fluidic group according to claim 5, wherein the first body (59) has a first surface (59') faceable to the second container (22), wherein the first hollow needle (60) is supported in a releasable manner by a first support portion (152) of the first body (59) extending starting from, and perpendicular to, said first surface (59'), wherein the first hollow needle (60) has a first (60a) and a second (60b) end opposite to each other, the second end (60b) being fixed to the first tubular element (62), and wherein the first hollow needle (60) is supported by the first support portion (152) so that the second end (60b) is faceable to the first surface (59') and the first end (60a) is faceable to the first cap (24b) of the first container (24).

7. The fluidic group according to claim 1, wherein the first coupling group (171, 172) comprises a second support portion (171b) fixed to the first body (59), extending outside the first cavity (59a) and configured to support the second container (22), the second support portion (171b) including a second hollow needle (171a) in fluid communication with the first inlet (166') through the first valve (168), the second hollow needle (171a) being insertable in a second cap (22b) of the second container (22) so as to allow said fluid communication between the second internal volume and said chamber (162a) of the syringe (154).

8. An apparatus (1) for drug preparation starting from at least one ingredient, the apparatus (1) being characterized in that it comprises:

a first support element (11), configured to support at least one first container (24) adapted to contain the drug and arrangeable, in a releasable manner, on the first support element (11);

at least one fluidic group (21) according to claim 1;

a second support element (9), supporting the at least one fluidic group (21), said at least one fluidic group (21) being arranged, in a releasable manner, on the second support element (9) and being couplable in a releasable manner with a respective second container (22) adapted to contain a respective said ingredient;

a control unit (83);

connection means (70), couplable to the first container (24) and to the second container (22) and operatively coupled to the control unit (83), said connection means (70) being controllable by the control unit (83) so as to couple the second coupling group (25) with the first container (24) to fluidically connect the second container (22) to the first container (24); and pumping means (80), coupled to the fluidic group (21) and operatively coupled to the control unit (83), said pumping means (80) being controllable by the control unit (83) so as to transfer, at least partially, the ingredient from the second container (22) into the first container (24).

9. The apparatus according to claim 8, further comprising a base (3) having a second surface (3a) to which the first support element (11) and the second support element (9) are coupled, the first support element (11) and the second support element (9) extending parallel to said second surface (3*a*) and being arranged coaxially to each other relative to a rotation axis (15) perpendicular to the second surface (3*a*), and the second support element (9) being axially interposed, relative to the rotation axis (15), between the first support element (11) and the second surface (3*a*), and being rotatable relative to the base (3) about the rotation axis (15).

10. The apparatus according to claim 9, wherein the second support element (9) is rotatable relative to the base (3) about the rotation axis (15) and is configured to support, in a releasable manner, the second container (22) through the fluidic group (21), and at least a further second container (22) through a further fluidic group (21).

11. The apparatus according to claim 9, wherein the first support element (11) is rotatable relative to the base (3) about the rotation axis (15) and is configured to support, in a releasable manner, the first container (24) and at least a further first container (24).

12. The apparatus according to claim 10, further comprising first operating means (27) controllable by the control unit (83) and configured to rotate, independently of each other, the first support element (11) and the second support element (9) relative to the base (3) about the rotation axis (15), so that a first selected container (24) and a second selected container (22) are arrangeable in respective angular positions so that they are facing the connection means (70) and the pumping means (80).

13. The apparatus according to claim 9, wherein the connection means (70) comprise:
  a first guide element (73), fixed to the base (3) and defining a first path parallel to a first axis (Z);
  a first movable element (75), coupled with the first guide element (73) so as to move along said first path; and
  a first gripping means (74), fixed to the first movable element (75) and controllable by the control unit (83) to couple, in a releasable manner, with the second coupling group (25),
  wherein the connection means (70) are controllable by the control unit (83) to couple, through the first gripping means (74), with the second coupling group (25) and, subsequently, to move the second coupling group (25) along the first path so as to couple the second coupling group (25) with the first container (24) creating a connection with passage of fluid.

14. The apparatus according to claim 13, wherein the pumping means (80) include:
  a second guide element (273), fixed to the base (3) and defining a second path parallel to a second axis (X) orthogonal to the first axis (Z);
  a second movable element (275), coupled with the second guide element (273) so as to move along said second path; and
  a second gripping means (274), fixed to the second movable element (275) and controllable by the control unit (83) to couple, in a releasable manner, with the piston (150),
  wherein the pumping means (80) are controllable by the control unit (83) to couple, by means of the second gripping means (274), with the piston (150) and, subsequently, to move the second movable element (275) relative to the second guide element (273) along the second path, moving the piston (150) in the second cavity (158) and generating the first pressure gradient or the second pressure gradient.

15. The apparatus according to claim 14,
  wherein the second body (156) has a first (156*a*) and a second (156*b*) end portion opposite each other, the chamber (162*a*) being fluidically connected to the third inlet (166''') at said first end portion (156*a*),
  wherein the piston (150) comprises a seal element (150') defining with the second body (156) said chamber (162*a*) and sliding in a fluid-tight manner in the second body (156) between a first position and a second position relative to the second body (156),
  wherein, when the seal element (150') is in the first position, the seal element (150') has a first distance from the first end portion (156*a*) of the second body (156) and the chamber (162*a*) has a first volume,
  wherein, when the seal element (150') is in the second position, the seal element (150') has a second distance from the first end portion (156*a*) of the second body (156) and the chamber (162*a*) has a second volume, the second distance being greater than the first distance and the second volume being greater than the first volume,
  wherein the first valve (168) is operable to pass from a first closing state to a first opening state and the second valve (176) is operable to pass from a second closing state to a second opening state,
  wherein the pumping means (80) are controllable by the control unit (83) to move the seal element (150') from the first position to the second position, the first pressure gradient exerting a force such that the first valve (168) is in the first opening state and the second valve (176) is in the second closing state to allow passage of the ingredient from the second container (22) into the chamber (162*a*) of the syringe (154),
  and wherein the pumping means (80) are controllable by the control unit (83) to move the seal element (150') from the second position to the first position, the second pressure gradient exerting a further force such that the first valve (168) is in the first closing state and the second valve (176) is in the second opening state to allow the passage, from the chamber (162*a*) of the syringe (154) to the first container (24), of the ingredient transferred from the second container (22) to the chamber (162*a*).

16. The apparatus according claim 8, wherein the control unit (83) is operatively coupled to a printing apparatus (85") controllable by the control unit (83) to generate a label adapted to be coupled with the first container (24) and identifying said drug.

\* \* \* \* \*